(12) United States Patent
Spratt et al.

(10) Patent No.: US 9,468,371 B2
(45) Date of Patent: Oct. 18, 2016

(54) STATISTICAL AUTOREFRACTOR

(71) Applicants: Carl Zeiss Vision Inc., San Diego, CA (US); Carl Zeiss Vision International GmbH, Aalen (DE)

(72) Inventors: Ray Steven Spratt, Petaluma, CA (US); Timo Kratzer, Aalen (DE)

(73) Assignees: Carl Zeiss Vision International GmbH, Aalen (DE); Carl Zeiss Vision, Inc., San Diego, CA (US)

( * ) Notice: Subject to any disclaimer, the term of this patent is extended or adjusted under 35 U.S.C. 154(b) by 100 days.

(21) Appl. No.: 14/249,645

(22) Filed: Apr. 10, 2014

(65) Prior Publication Data

US 2014/0218681 A1  Aug. 7, 2014

Related U.S. Application Data

(63) Continuation of application No. PCT/EP2011/056517, filed on Oct. 17, 2011.

(51) Int. Cl.
A61B 3/10 (2006.01)
A61B 3/00 (2006.01)
A61B 3/103 (2006.01)
G02C 7/02 (2006.01)
A61B 3/028 (2006.01)
G06F 19/00 (2011.01)

(52) U.S. Cl.
CPC ........... *A61B 3/1015* (2013.01); *A61B 3/0025* (2013.01); *A61B 3/103* (2013.01); *G02C 7/027* (2013.01); *A61B 3/028* (2013.01); *G02C 2202/22* (2013.01); *G06F 19/3481* (2013.01)

(58) Field of Classification Search
USPC .................................................. 351/205, 246
See application file for complete search history.

(56) References Cited

U.S. PATENT DOCUMENTS

| 7,857,451 | B2 | 12/2010 | Thibos et al. |
|---|---|---|---|
| 2003/0081174 | A1 | 5/2003 | Ross et al. |
| 2004/0263786 | A1 | 12/2004 | Williams et al. |
| 2005/0200809 | A1 | 9/2005 | Dreher et al. |
| 2007/0115432 | A1 | 5/2007 | Thibos et al. |
| 2009/0006508 | A1 | 1/2009 | Youssefi et al. |

(Continued)

FOREIGN PATENT DOCUMENTS

| CN | 1635848 A | 7/2005 |
|---|---|---|
| CN | 101224103 | 7/2008 |

(Continued)

OTHER PUBLICATIONS

International Report on Patentability for corresponding PCT Appl No. PCT/EP2011/056517, mailed Apr. 22, 2014.

(Continued)

*Primary Examiner* — Jack Dinh
(74) *Attorney, Agent, or Firm* — Fish & Richardson P.C.

(57) ABSTRACT

Methods for determining a prescription (Rx) for a person include providing aberrometric data characterizing wavefront errors of the person's eye, the aberrometric data being obtained using an wavefront sensor and comprising one or more coefficients characterizing the wavefront errors; determining a starting Rx for the person's eye based on the one or more coefficients and on predetermined information relating aberrometric data and subjective refraction data for a plurality of people's eyes; and reporting the starting Rx to an eye care professional.

20 Claims, 2 Drawing Sheets

(56) References Cited

U.S. PATENT DOCUMENTS

| | | |
|---|---|---|
| 2009/0066915 A1 | 3/2009 | Lai |
| 2009/0161071 A1 | 6/2009 | Dreher et al. |
| 2010/0182566 A1 | 7/2010 | Becker et al. |

FOREIGN PATENT DOCUMENTS

| | | |
|---|---|---|
| WO | 2008/049503 | 5/2008 |
| WO | 2010/065475 | 6/2010 |

OTHER PUBLICATIONS

International Search Report and Written Opinion for corresponding PCT Appl No. PCT/EP2011/056517, mailed Feb. 1, 2012.

Extended European Search Report of the European Patent Office for Application No. 11874327.7 dated Aug. 7, 2015, 7 pages.

Chinese Office Action, with translation thereof, for CN Appl No. 201180074225.6, dated Jul. 31, 2015.

Chinese Office Action, with translation thereof, for corresponding CN Appl No. 201180074225.6, dated Apr. 15, 2016.

STATISTICAL AUTOREFRACTOR

CROSS-REFERENCE TO RELATED APPLICATIONS

The present application is a continuation of, and claims benefit under 35 U.S.C. 120 to, International Application PCT/EP2011/056517, filed Oct. 17, 2011. The entire disclosure of International Application PCT/EP2011/056517 is incorporated by reference herein.

TECHNICAL FIELD

This invention relates to autorefractors and determining a prescription based on wavefront sensor measurements.

BACKGROUND

An automated refractor, or "autorefractor," is a computer-controlled machine used during an eye examination to provide an objective measurement of a person's refractive error and prescription ("Rx") for glasses or contact lenses. This is achieved by measuring how light is changed as it enters a person's eye. Autorefractors are commercially-available from Unicos USA LLC (Miami, Fla.), Topcon (Oakland, N.J.), Tomey (Phoenix, Ariz.), and Carl Zeiss Vision, Inc. (San Diego, Calif.), for example.

Wavefront sensors (also known as "wavefront aberrometers") are a type of instrument that measure wavefront errors of a person's eye (e.g., second and higher order Zernike coefficients). A variety of techniques exist for determining an Rx from the wavefront errors. In some approaches, model-based techniques are used. Such techniques can use optical simulation software (e.g., ray-tracing software) to establish a second-order (e.g., power and astigmatism) correction suitable for the measured eye based on the measured wavefront errors. In many cases, the Rx calculated from the wavefront errors is not the same as an Rx determined for a person using a subjective refraction. Examples of commercially-available wavefront sensors include the i.Profiler$^{plus}$®, from Carl Zeiss Vision, Inc.

A common use for an autorefractor is to give an optometrist starting values for the sphere, cyl, and axis (or, correspondingly, M, $J_0$, and $J_{45}$) for performing a subjective refraction. The final Rx for that person is then determined using the subjective refraction. In general, the closer the starting values are to the final prescription, the less time the optometrist spends in finding the final Rx.

SUMMARY

Techniques are disclosed for determining an Rx from an autorefraction using wavefront errors. These techniques can be used to establish a starting Rx for a subjective refraction based on a wavefront sensor measurement and also based on predetermined data relating wavefront measurements and subjective refraction measurements of a large set (e.g., large enough to draw meaningful statistical data) of eyes. Rx's calculated for a person using the disclosed techniques are, in general, better correlated to the person's Rx determined using a subjective refractive than conventional (e.g., model-based) wavefront calculations.

In certain implementations, an expression for second order aberration corrections for a person is formulated to decouple the scaling coefficients for various Zernike terms. These coefficients are then adjusted to replicate the results of subjective refractions using a data set of measured eyes. The result is an autorefraction that is better correlated with subjective refraction results than conventional model-based methods. Accordingly, where an optometrist (or other eye care professional) uses an autorefraction as a starting point for a subjective refraction, the final Rx based on the subjective refraction may be more quickly obtained.

In general, in one aspect, the invention features methods for determining a prescription (Rx) for a person, that include providing aberrometric data characterizing wavefront errors of the person's eye, the aberrometric data being obtained using an wavefront sensor and comprising one or more Zernike coefficients; determining a starting Rx for the person's eye based on the one or more Zernike coefficients and on predetermined information relating aberrometric data and subjective refraction data for a plurality of people's eyes; and reporting the starting Rx to an eye care professional.

Implementations of the methods can include one or more of the following features. For example, the methods can include determining a final Rx for the person from a subjective refraction, wherein the subjective refraction using the starting Rx as a starting point. The predetermined information can reduce (e.g., minimize) variations between an Rx determined using a subjective refraction and an Rx determined using a wavefront sensor for each of the plurality of people. The predetermined information can include one or more scaling values and determining the starting Rx comprises scaling one or more of the Zernike coefficients with a corresponding scaling factor. Each component of the starting Rx can be determined as a linear combination of Zernike coefficients scaled with the corresponding scaling factor.

In some embodiments, the aberrometric data comprises second order Zernike coefficients for the person and a dimension of the person's pupil, and determining the starting Rx comprises scaling the second (and/or higher) order Zernike coefficients based on the dimension and the predetermined data. The dimension can be the radius of the person's pupil. The scaling can be based on a linear combination of the second order Zernike coefficients and higher order coefficients. The mean power (M) and cyl ($J_0$, $J_{45}$) components of the starting Rx can be determined according to an expression having the form:

$$M = f(r) \sum_{n,m} c_m^n m_n$$

$$J_i = g_i(r) \sum_{n,m} c_m^n j_n,$$

where $m_n$ and $j_n$ are scaling factors relating autorefraction data and subjective refraction data for the plurality of people for coefficients $c_n^m$ of the Zernike expansion of a wavefront error as defined according to the ANSI Z-80 standard, n is a non-negative integer greater than one, m is an integer from −n to +n in steps of 2, f and $g_i$ are functions of the radius of the person's pupil, r, and i is 0 or 45.

In some embodiments, the mean power (M) and cyl ($J_0$, $J_{45}$) components of the starting Rx, in units of diopter, are determined according to the following equations:

$$M = \frac{-4\sqrt{3}}{r^2}[c_2^0 m_2 + c_4^0 m_4 + c_6^0 m_6]$$

$$J_0 = \frac{-2\sqrt{6}}{r^2}[c_2^2 j_2 + c_4^2 j_4 + c_6^2 j_6]$$

-continued $$J_{45} = \frac{-2\sqrt{6}}{r^2}[c_2^{-2}j_2 + c_4^{-2}j_4 + c_6^{-2}j_6],$$

where $m_n$ and $j_n$ are scaling factors relating autorefraction data and subjective refraction data for the plurality of people for coefficients $c_n^m$ of the Zernike expansion of a wavefront error as defined according to the ANSI Z-80 standard, n is a non-negative integer greater than one, m is an integer from −n to +n in steps of 2, and r is the radius of the person's pupil.

In certain embodiments, the predetermined data is determined based on wavefront sensor measurements and subjective refractions for a sufficiently large number of people for the data to be statistically accurate (e.g., at least 10,000 different people).

In general, in another aspect, the invention features systems for determining a starting Rx for a subjective refraction, including a wavefront sensor, and an electronic processing module in communication with the wavefront sensor and arranged to receive aberrometric data characterizing wavefront errors of a person's eye obtained using the wavefront sensor, the aberrometric data comprising one or more Zernike coefficients. The electronic processing module is programmed to determine the starting Rx for the person's eye based on the one or more Zernike coefficients and on predetermined information relating aberrometric data and subjective refraction data for a plurality of people's eyes.

Implementations of the system can include one or more of the following features. For example, the system can further include a memory module in communication with the electronic processing module, the memory module containing the predetermined data relating aberrometric data and subjective refraction data for the plurality of people's eyes. The predetermined data can be in the form of a lookup table. The electronic processing module can be programmed to output the starting Rx.

The details of one or more embodiments are set forth in the accompanying drawings and the description below. Other features and advantages will be apparent from the description and drawings, and from the claims.

DETAILED DESCRIPTION

Figure 1:
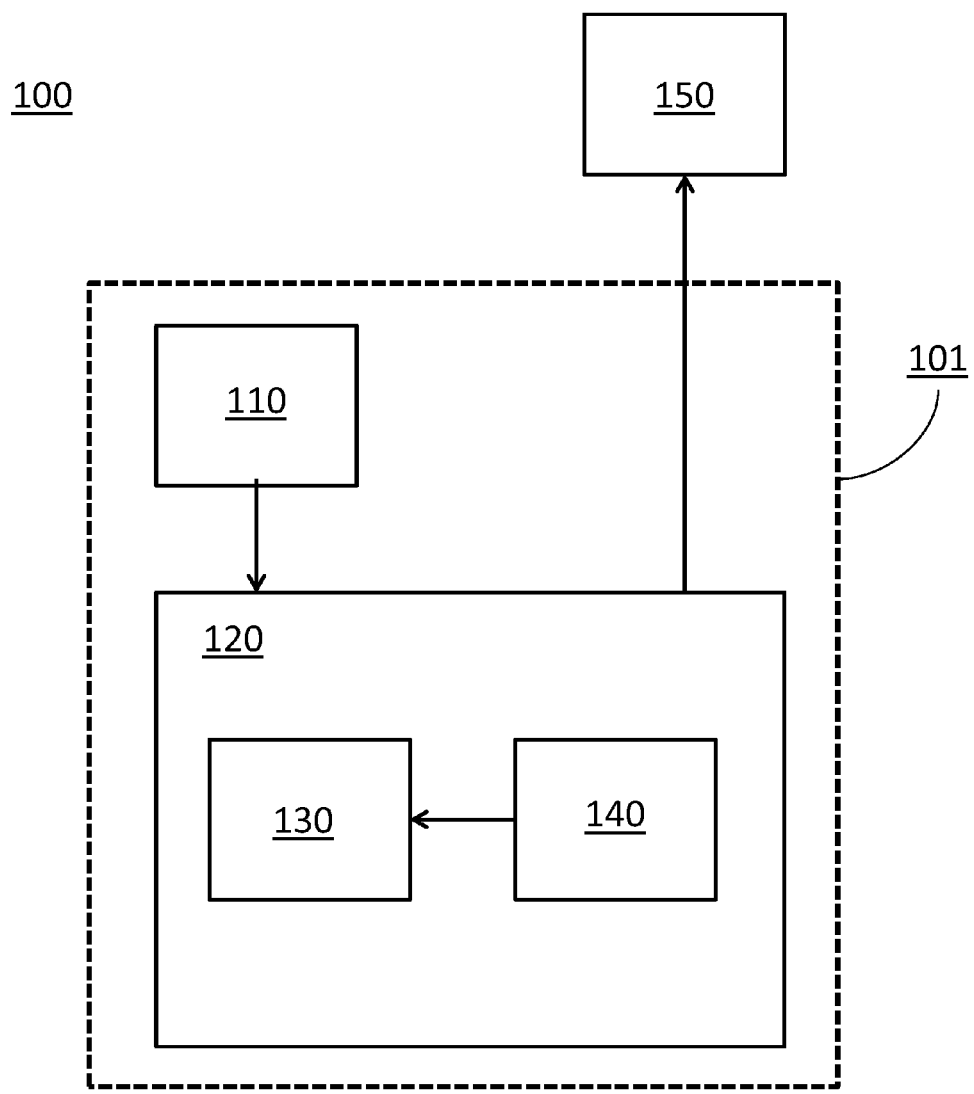
FIG. 1 is a schematic diagram of an embodiment of a system for determining an Rx using a statistical autorefractor.

Referring to FIG. 1, a system 100 for determining an Rx for a person includes a wavefront sensor 110 (e.g., a commercially-available wavefront sensor) and a refractor 150 (e.g., a phoropter). Wavefront sensor 110 is in electronic communication with an electronic processing system 120, which is programmed to analyze data from the wavefront sensor. Together, wavefront sensor 110 and electronic processing system 120, form a statistical autorefractor 101. An eyecare professional uses the wavefront sensor 110 to perform a wavefront measurement of a person's eye to determine information about wavefront errors of the person's eye. For example, wavefront sensor 110 can determine values for Zernike coefficients for a wavefront for each of the person's eye. This information is sent from wavefront sensor 110 to electronic processing system 120, where electronic processing system 120 uses the information to determine a starting Rx for a subjective refraction for the person. Electronic processing system 120 outputs the starting Rx to the eyecare professional, who then performs a subjective refraction on the person's eye using refractor 150.

Electronic processing system 120 includes an electronic processing module 130 (e.g., composed of one or more computer processors) and a memory module 140 (e.g., composed of RAM or ROM). Memory module 140 contains predetermined data relating wavefront measurements and subjective refraction measurements of a large population of people's eyes (e.g., 10,000 or more eyes). Electronic processing module 130 accesses the predetermined data in memory module 140 and performs operations (e.g., arithmetic and/or logical operations) on data received from wavefront sensor 110 to determine the starting Rx for the person.

The predetermined data is compiled from prior wavefront sensor measurements and subjective refraction measurements of people's eyes. The data can be pooled from more than one eye care professionals practice. The data can include additional information beyond simply the wavefront sensor measurements and subjective refraction measurements. For example, the data can include physiological information about each person (e.g., pupil radius, the person's age, medical history) and/or demographic information (e.g., information about each person's race, geographic location)

In general, the predetermined data can be stored in a variety of forms. For example, in some embodiments, the data is in the form of one or more lookup tables. In certain implementations, electronic processing system 120 retrieves a starting Rx directly from the lookup table based on the wavefront error measurement, e.g., based on the values of one or more Zernike coefficients characterizing the wavefront error. In some embodiments, a lookup table includes a series of values for factors used to appropriately scale Zernike coefficients to provide the starting Rx (examples of such coefficients are discussed below). Alternatively, or additionally, the predetermined data can include functional data established based on the prior wavefront sensor and subjective refraction measurements, where the functional data is used to calculate a starting prescription from the information about the wavefront errors based on one or more analytic equations relating the Rx and the wavefront errors.

In general, the components of electronic processing system 120 can be housed in a common housing. For example, electronic processing system 120 can a personal computer, e.g., supplied with wavefront sensor 110. In some embodiments, the components of electronic processing system 120 are housed separately. For example, electronic processing module 130 can part of a personal computer located at the eyecare professional's office, and memory module can be housed elsewhere. The components can be connected via a network (e.g., the internet). In certain embodiments, memory module 140 is shared between many electronic processing systems, and can be updated by a third party as additional data about people's eyes becomes available.

Figure 2:
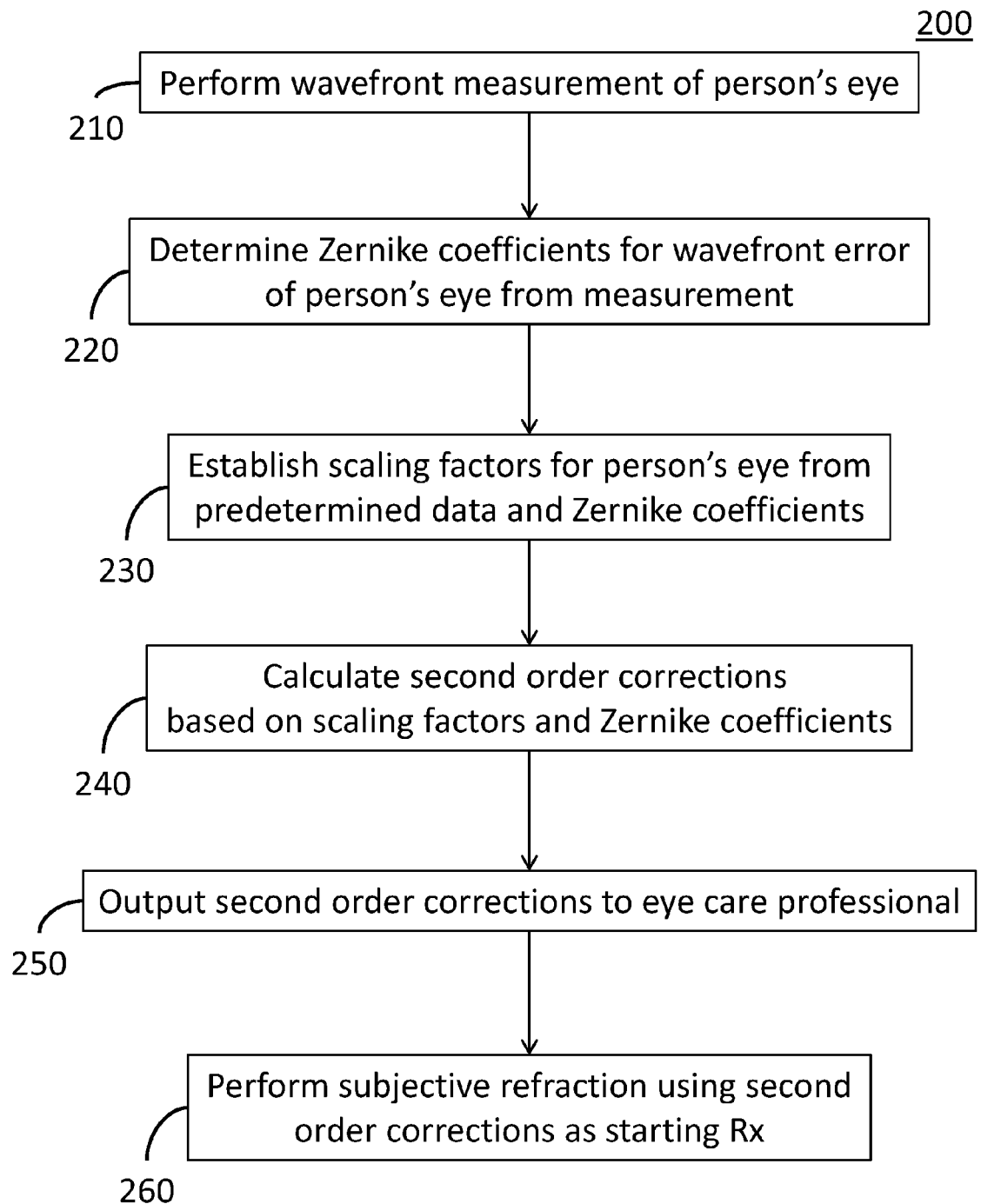
FIG. 2 is a flow chart of a method for determining an Rx using a statistical autorefractor Like reference symbols in the various drawings indicate like elements.

Referring to FIG. 2, a method 200 for determining the starting Rx includes the following steps. First, the eyecare professional performs a measurement of the wavefront errors of the person's eyes (step 210). The wavefront sensor determines Zernike coefficients for the wavefront error of the person's eye (step 220). This step can be performed by an electronic processing module within the wavefront sensor itself, or measurement data (e.g., unprocessed intensity measurements) can be sent from the wavefront sensor to an electronic processing module in a separate system, where Zernike coefficients are determined.

Next, the algorithm establishes scaling factors for the person's eye based on the Zernike coefficients and predetermined data stored in the memory module (step 240). The scaling factors are coefficients of equations that relate the Zernike coefficients to the second order corrections characterizing the Rx (e.g., mean power, cyl, and axis, or M, $J_0$, and $J_{45}$). The scaling factors can be determined, for example, from a lookup table that associates values of the scaling factors with values of the Zernike coefficients.

The electronic processing module then calculates second order corrections based on the scaling factors and the Zernike coefficients (step 240).

The electronic processing system outputs the second order corrections to the eyecare professional (step 250) who then uses the second order corrections as a starting Rx for performing a subjective refraction on the person (step 260). Because the starting Rx is calculated based on the predetermined data, it can provide a more accurate starting Rx than autorefraction methods that don't use predetermined data, such as methods that rely purely on models.

Outputting the second order corrections can involve displaying the correction values on an electronic display or printing them out on paper, for example. Alternatively, or additionally, outputting can involve transmitting them electronically directly to the refractor, or transmitting them over a network (e.g., to another eyecare professional at a different location, e.g., via e-mail).

Without wishing to be bound by theory, it is instructive to consider various techniques for determining a starting Rx from autorefraction data that do not involve scaling the measured Zernike coefficients based on predetermined information relating autorefraction data and subjective refraction data for a sampling of people.

For example, in some approaches, the second order corrections for the aberrations of a person's eye can be estimated from a wavefront measurement by simply appropriately scaling the corresponding second order Zernike coefficient. For example, the resulting expressions for the three second order correction components may be expressed as:

$$M = \frac{-c_2^0 4\sqrt{3}}{r^2}, \quad \text{Eq. (1)}$$

$$J_0 = \frac{-c_2^2 2\sqrt{6}}{r^2},$$

and $$J_{45} = \frac{-c_2^{-2} 2\sqrt{6}}{r^2},$$

where M is the mean power scaled directly from the Zernike coefficient $c_2^0$, $J_0$ and $J_{45}$ are the astigmatic corrections where $J_0$ is scaled directly from the $c_2^2$ Zernike coefficient, and $J_{45}$ is scaled directly from the $C_2^{-2}$ Zernike coefficient. Here, $c_n^m$ are the coefficients of the Zernike expansion of the wavefront error as detailed by the ANSI Z-80 standard, and r is the radius of the pupil. The Zernike coefficients and pupil radius are provided by the wavefront sensor and the scaling factors provide values for M, $J_0$ and $J_{45}$ in diopters.

More generally, the three second order correction components can be expressed in other ways, e.g., as sphere, cylinder, and axis.

As a further example, and as a refinement to the above expressions, one can use second order Zernike terms for a pupil radius r' smaller than that of the full pupil measured. In this case, the expressions for M, $J_0$, and $J_{45}$, to sixth order, are:

$$M = \frac{-4\sqrt{3}}{r^2}\left[c_2^0 + c_4^0\sqrt{15}(\gamma^2 - 1) + c_6^0\sqrt{21}(3\gamma^{-1} - 5\gamma^2 + 2)\right] \quad \text{Eq. (2)}$$

$$J_0 = \frac{-2\sqrt{6}}{r^2}\left[c_2^2 + c_4^2\sqrt{15}(\gamma^2 - 1) + c_6^2\sqrt{21}(3\gamma^4 - 5\gamma^3 + 2)\right]$$

$$J_{45} = \frac{-2\sqrt{6}}{r^2}\left[c_2^{-2} + c_4^2\sqrt{15}(\gamma^2 - 1) + c_6^{-2}\sqrt{21}(3\gamma^4 - 5\gamma^2 + 2)\right]$$

Here, $\gamma = r'/r$ and $c_n^m$ are the coefficients calculated for the full radius r.

In certain embodiments, autorefraction algorithms use the second order Zernike coefficients with a maximum pupil radius of 3 mm. In other words, if the measured pupil is less than 3 mm, then the full pupil is used (i.e., the first set of equations for M, $J_0$, and $J_{45}$, above, are used). If the pupil is greater than 3 mm in radius, then the pupil is scaled back, e.g., using the second set of equations for M, $J_0$, and $J_{45}$. However, such a scaling does not necessarily produce an Rx identical to the Rx determined for a person using subjective refraction. Algorithms based on other pupil radii (i.e., different from 3 mm) are contemplated.

Table 1 below shows differences between values calculated using the above set of equations and the results of subjective refractions performed for 42,400 eyes. The values tabulated for the mean power are the absolute value for the difference in mean power $|\Delta M|$, and for the cyl they are the vector differences in total cyl, $2\sqrt{(\Delta J_0)^2 + (\Delta J_{45})^2}$; both in diopters. The differences between the autorefraction determined values and the subjectively determined values are shown for the $50^{th}$, $75^{th}$, $90^{th}$, $95^{th}$, and $99^{th}$ percentiles, respectively. This means, for example, that half of the eyes in the sample set have autorefraction estimated cyls that were within 0.25 diopters of the subjectively determined cyl for the same eye, and 99% are within 0.77 diopters.

In some cases, the results of the subjective refractions in the same set are taken into account by finding a sub-radius, r', that minimizes differences between the estimated corrections and the corrections from subjective refractions. The optimal sub-radius can be estimated in a variety of ways. For example, the sub-radius that minimizes the average mean power difference is 4.0 mm, while the sub-radius that minimizes the average cyl differences is 3.5 mm. The results of using those two radii are summarized in Table 1 below as well. However, a comparison of those results with the 3 mm results shoes that little has been gained.

TABLE 1

| Percentile (%) | Cyl | | | Mean Power | | |
|---|---|---|---|---|---|---|
| | 3 mm | 4 mm | Statistical | 3 mm | 3.5 mm | Statistical |
| 50 | 0.25 | 0.24 | 0.22 | 0.18 | 0.18 | 0.17 |
| 75 | 0.40 | 0.38 | 0.36 | 0.33 | 0.32 | 0.30 |
| 90 | 0.60 | 0.58 | 0.53 | 0.52 | 0.51 | 0.47 |
| 95 | 0.77 | 0.74 | 0.68 | 0.69 | 0.68 | 0.62 |
| 99 | 1.33 | 1.31 | 1.19 | 1.59 | 1.58 | 1.43 |

In the embodiments disclosed above, however, instead of locking the scaling of the various relevant Zernike components to a theoretical model (e.g., as for the second set of equations, above), the scaling factors can be allowed to vary and take on values that reduce (e.g., minimize) differences between the estimated corrections and the subjectively determined corrections. As a specific example, in some embodiments, equations having the the following form can be used to determine M, $J_0$, and $J_{45}$:

$$M = \frac{-4\sqrt{3}}{r^2}[c_2^0 m_2 + c_4^0 m_4 + c_6^0 m_6] \qquad \text{Eq. (3)}$$

$$J_0 = \frac{-2\sqrt{6}}{r^2}[c_2^2 j_2 + c_4^2 j_4 + c_6^2 j_6]$$

$$J_{45} = \frac{-2\sqrt{6}}{r^2}[c_2^{-2} j_2 + c_4^{-2} j_4 + c_6^{-2} j_6].$$

Here, $m_n$ and $j_n$, n=2, 4, 6, are coefficients determined specifically from the predetermined data.

The values for the coefficients that minimize the mean power and cyl errors for a eye data set compiled from measurements of 42,000 eyes are provided in Table 2, below. These values were established as the coefficients that minimized the differences between the starting Rx and the final Rx for the 90% percentile.

TABLE 2

| $m_2$ | $m_4$ | $m_6$ | $j_2$ | $j_4$ | $j_6$ |
|---|---|---|---|---|---|
| 0.96 | −1.6 | 0.8 | 0.88 | −1.2 | 0.8 |

The resulting percentile differences are presented in Table 1, above, in the columns labeled "Statistical." The differences are consistently smaller than those established using the prior equations (i.e., the values shown in the columns "3 mm", "4 mm" and "3.5 mm" in Table 1), particularly at higher percentiles. Accordingly, in certain embodiments, a starting Rx is determined in accordance with Eq. (3) using the parameter values provided in Table 2.

More generally, other forms of equations can be used to establish second order correction terms for a starting Rx based on Zernike coefficients. For example, in some embodiments, higher order Zernike coefficients are used in addition to those in Eq. (3). Generally, equations of the following form may be used:

$$M = f(r) \sum_{n,m} c_m^n m_n \qquad \text{Eq. (4)}$$

$$J_i = g_i(r) \sum_{n,m} c_m^n j_n$$

where $m_n$ and $j_n$ are predetermined scaling factors relating autorefraction data and subjective refraction data for the plurality of people for coefficients $c_n^m$ of the Zernike expansion of a wavefront error as defined according to the ANSI Z-80 standard, n is a non-negative integer greater than one, m is an integer from −n to +n in steps of 2, f and $g_i$ are functions of the radius of the person's pupil, r, and i is 0 or 45.

Moreover, in certain implementations, the predetermined data used to establish the starting Rx can be periodically updated. For example, once the eyecare professional determines a final Rx for a person, using a starting Rx established using the aforementioned techniques, the predetermined data can be updated to include the starting and final Rx's for that person.

Furthermore, while the foregoing embodiments use Zernike coefficients to characterize wavefront errors, implementations using alternate expansions of a wavefront error are also possible. For example, in some embodiments, Seidel aberrations can be used to characterize wavefront errors. In such implementations, one could construct a different set of scaling factors for Seidel aberrations that would in the same manner as the ones for the Zernike aberrations discussed above. As would be understood by a person having ordinary skill in the art, similar results for any linearly independent set of functions used to expand the wavefront would be expected.

A number of embodiments have been described. Other embodiments are in the following claims.

What is claimed is:

1. A method for determining a prescription (Rx) for a person, comprising:
   providing aberrometric data characterizing wavefront errors of the person's eye, the aberrometric data being obtained using a wavefront sensor and comprising one or more coefficients characterizing the wavefront errors;
   determining the prescription (Rx) for the person's eye based on the one or more coefficients and on predetermined information relating aberrometric data for a plurality of people's eyes and corresponding subjective refraction data for the plurality of people's eyes, the corresponding subjective refraction data comprising subjectively determined corrections for the plurality of people's eyes; and
   reporting the prescription (Rx) to an eye care professional, wherein the predetermined information is determined based on
   i) estimated corrections for the plurality of people's eyes, each of the estimated corrections being characterized by one or more coefficients derived from the aberrometric data for the plurality of people's eyes and one or more scaling factors corresponding to each of the one or more coefficients; and
   ii) the corresponding subjectively determined corrections for the plurality of people's eyes,
   the predetermined information comprises values for the one or more scaling factors, the scaling factors have been varied in a previous process to take on values that minimize differences between the estimated corrections for the plurality of people's eyes and the corresponding subjectively determined corrections for the plurality of people's eyes, and
   determining the prescription (Rx) comprises scaling the one or more of the coefficients characterizing the wavefront errors with the values of the one or more scaling factors that minimize differences between the estimated corrections for the plurality of people's eyes and the corresponding subjectively determined corrections for the plurality of people's eyes.

2. The method of claim 1, wherein each component of the prescription (Rx) is determined as a linear combination of the coefficients scaled with the one or more scaling factors.

3. The method of claim 1, wherein the aberrometric data comprises second order Zernike coefficients for the person and a dimension of the person's pupil, and determining the prescription (Rx) comprises scaling the second order Zernike coefficients based on at least the dimension and the predetermined information.

4. The method of claim 3, wherein the dimension is the radius of the person's pupil.

5. The method of claim 3, wherein the scaling is based on a linear combination of the second order Zernike coefficients and higher order coefficients.

6. The method of claim 1, further comprising providing information characterizing a dimension of the person's pupil; and wherein determining the prescription (Rx) for the person's eye is further based on the dimension of the person's pupil.

7. The method of claim 6, wherein determining the prescription (Rx) comprises scaling one or more of the coefficients with the one or more scaling factors.

8. The method of claim 7, wherein each component of the prescription (Rx) is determined as a linear combination of the coefficients scaled with the one or more scaling factors.

9. The method of claim 6, wherein the aberrometric data comprises second order Zernike coefficients for the person, and
determining the prescription (Rx) comprises scaling the second order Zernike coefficients based on at least the dimension of the person's pupil and the predetermined information.

10. A system for determining a prescription (Rx) for a person, the system comprising:
a wavefront sensor; and
an electronic processing module in communication with the wavefront sensor and arranged to receive aberrometric data characterizing wavefront errors of a person's eye obtained using the wavefront sensor, the aberrometric data comprising one or more coefficients characterizing the wavefront errors,
the electronic processing module being programmed to determine the prescription (Rx) for the person's eye based on the one or more coefficients and on predetermined information, the electronic processing module is configured to receive statistical aberrometric data for a plurality of people's eyes and corresponding subjective refraction data for the plurality of people's eyes, the corresponding subjective refraction data comprising subjectively determined corrections for the plurality of people's eyes, the predetermined information is based on
i) estimated corrections for the plurality of people's eyes, each of the estimated corrections being characterized by one or more coefficients derived from the statistical aberrometric data for the plurality of people's eyes and one or more scaling factors corresponding to each of the one or more coefficients; and
ii) the corresponding subjectively determined corrections for the plurality of people's eyes,
the predetermined information comprises values for the one or more scaling factors, the scaling factors being varied in a previous process so that the scaling factors take on values that minimize differences between the estimated corrections for the plurality of people's eyes and the corresponding subjectively determined corrections for the plurality of people's eyes, wherein the plurality of people's eyes comprises at least 10,000 people's eyes, and
the electronic processing module being programmed to determine the prescription (Rx) comprises scaling the one or more of the coefficients characterizing the wavefront errors with the values of the one or more scaling factors that minimize differences between the estimated corrections for the plurality of people's eyes and the corresponding subjectively determined corrections for the plurality of people's eyes.

11. The system of claim 10, wherein determining the prescription (Rx) comprises scaling one or more of the coefficients with the one or more scaling factors.

12. The system of claim 11, wherein each component of the prescription (Rx) is determined as a linear combination of the coefficients scaled with the one or more scaling factors.

13. The system of claim 10, wherein the aberrometric data comprises second order Zernike coefficients for the person and a dimension of the person's pupil, and
determining the prescription (Rx) comprises scaling the second order Zernike coefficients based on at least the dimension and the predetermined information.

14. The system of claim 10, wherein the prescription is a starting prescription (Rx) for a subjective refraction.

15. A system for determining a prescription (Rx) for a person, the system comprising:
a wavefront sensor; and
an electronic processing module in communication with the wavefront sensor and arranged to receive aberrometric data characterizing wavefront errors of a person's eye obtained using the wavefront sensor, the aberrometric data comprising one or more coefficients characterizing the wavefront errors,
the electronic processing module being programmed to determine the prescription (Rx) for the person's eye based on the one or more coefficients and on predetermined information, the electronic processing module is configured to receive aberrometric data for a plurality of people's eyes and corresponding subjective refraction data for the plurality of people's eyes, the corresponding subjective refraction data comprising subjectively determined corrections for the plurality of people's eyes, the electronic processing module is receive the predetermined information, the predetermined information is determined based on
i) estimated corrections for the plurality of people's eyes, each of the estimated corrections being characterized by one or more coefficients derived from the aberrometric data for the plurality of people's eyes and one or more scaling factors corresponding to each of the one or more coefficients; and
ii) the corresponding subjectively determined corrections for the plurality of people's eyes,
the predetermined information comprises values for the one or more scaling factors, the scaling factors are varied in a previous process so that the scaling factors take on values that minimize differences between the estimated corrections for the plurality of people's eyes and the corresponding subjectively determined corrections for the plurality of people's eyes, and
wherein determining the prescription (Rx) comprises scaling the one or more of the coefficients characterizing the wavefront errors with the values of the one or more scaling factors that minimize differences between the estimated corrections for the plurality of people's eyes and the corresponding subjectively determined corrections for the plurality of people's eyes.

16. The system of claim 15, further comprising a device configured to obtain information about the dimension of the person's pupil the electronic processing module being programmed to determine the prescription (Rx) for the person's eye based also on the information about the dimension of the person's pupil.

17. The system of claim 16, wherein determining the prescription (Rx) comprises scaling one or more of the coefficients with the one or more scaling factors.

18. The system of claim 17, wherein each component of the prescription (Rx) is determined as a linear combination of the coefficients scaled with the one or more scaling factors.

19. The system of claim 16, wherein the aberrometric data comprises second order Zernike coefficients for the person, and
   determining the prescription (Rx) comprises scaling the second order Zernike coefficients based on at least the dimension of the person's pupil and the predetermined information.

20. A method for determining a prescription (Rx) for a person, the method comprising:
   providing aberrometric data characterizing wavefront errors of the person's eye, the aberrometric data being obtained using a wavefront sensor and comprising one or more coefficients characterizing the wavefront errors;
   determining the prescription (Rx) for the person's eye based on the one or more coefficients and on predetermined information relating statistical aberrometric data for a plurality of people's eyes and corresponding subjective refraction data for the plurality of people's eyes, the corresponding subjective refraction data comprising subjectively determined corrections for the plurality of people's eyes; and
   reporting the prescription (Rx) to an eye care professional, wherein the predetermined information is determined based on
   i) estimated corrections for the plurality of people's eyes, each of the estimated corrections being characterized by one or more coefficients derived from the statistical aberrometric data for the plurality of people's eyes and one or more scaling factors corresponding to each of the one or more coefficients; and
   ii) the corresponding subjectively determined corrections for the plurality of people's eyes,
   the predetermined information comprises values for the one or more scaling factors, the scaling factors being varied in a previous process so that the scaling factors take on values that minimize differences between the estimated corrections for the plurality of people's eyes and the corresponding subjectively determined corrections for the plurality of people's eyes, wherein the plurality of people's eyes comprises at least 10,000 people's eyes,
   determining the prescription (Rx) comprises scaling the one or more of the coefficients characterizing the wavefront errors with the values of the one or more scaling factors that minimize differences between the estimated corrections for the plurality of people's eyes and the corresponding subjectively determined corrections for the plurality of people's eyes.

* * * * *